United States Patent [19]
Barry

[11] Patent Number: 5,575,779
[45] Date of Patent: Nov. 19, 1996

[54] LIQUID REGULATOR AND METHOD OF USE

[75] Inventor: Robert L. Barry, Queensbury, N.Y.

[73] Assignee: Namic U.S.A. Corporation, Glens Falls, N.Y.

[21] Appl. No.: 366,692

[22] Filed: Dec. 30, 1994

[51] Int. Cl.$^6$ ................................ A61M 5/00
[52] U.S. Cl. .................. 604/246; 604/255; 604/122; 604/53
[58] Field of Search ................... 604/250–257, 604/122, 247, 180–185, 80, 83, 165–170, 28–34, 49–53; 222/52, 67, 481; 137/399, 590

[56] References Cited

U.S. PATENT DOCUMENTS

| | | |
|---|---|---|
| 2,710,004 | 6/1951 | Stamper . |
| 2,854,027 | 9/1958 | Kaiser et al. . |
| 2,866,457 | 12/1958 | Moore . |
| 3,001,397 | 9/1961 | Leonard . |
| 3,021,841 | 2/1962 | Burke . |
| 3,216,418 | 11/1965 | Scislowicz . |
| 3,216,419 | 11/1965 | Scislowicz . |
| 3,230,954 | 1/1966 | Burgess et al. . |
| 3,276,472 | 10/1966 | Jinkens et al. . |
| 3,664,339 | 5/1972 | Santomieri . |
| 3,667,464 | 6/1972 | Alligood, Jr. . |
| 3,756,237 | 9/1973 | Chittenden et al. . |
| 3,902,489 | 9/1975 | Carter . |
| 4,006,736 | 2/1977 | Kranys et al. . |
| 4,078,563 | 3/1978 | Tuseth . |
| 4,105,029 | 8/1978 | Virag . |
| 4,114,617 | 9/1978 | Turner et al. . |
| 4,175,558 | 11/1979 | Hers, III et al. . |
| 4,237,879 | 12/1980 | Genese . |
| 4,252,116 | 2/1981 | Genese et al. . |
| 4,256,104 | 3/1981 | Muetterties et al. . |
| 4,256,105 | 3/1981 | Leahey et al. . |
| 4,316,460 | 2/1982 | Genese et al. . |
| 4,332,247 | 6/1982 | Mittleman et al. . |
| 4,335,717 | 6/1982 | Bujan et al. . |
| 4,395,260 | 6/1983 | Todd et al. . |
| 4,397,648 | 8/1983 | Knute . |
| 4,432,756 | 2/1984 | Urquhart et al. . |
| 4,439,182 | 3/1984 | Huang . |
| 4,525,162 | 6/1985 | Urquhart et al. . |
| 4,576,592 | 3/1986 | Danby . |
| 4,601,712 | 7/1986 | Cole et al. . |
| 4,673,400 | 6/1987 | Martin . |
| 4,687,473 | 8/1987 | Raines . |
| 4,692,144 | 9/1987 | Carpenter . |
| 4,718,896 | 1/1988 | Arndt et al. . |
| 4,734,091 | 3/1988 | Boyle et al. . |
| 4,750,643 | 6/1988 | Wortich . |
| 4,834,705 | 5/1989 | Vaillancourt . |
| 4,915,689 | 4/1990 | Theeuwes . |

(List continued on next page.)

FOREIGN PATENT DOCUMENTS

WO88/03815   6/1988   WIPO .

OTHER PUBLICATIONS

Namic's In–Line System for Contrast Management.
Namic's Secondary Syringe System for Contrast Management.
Namic's Off–Line System for Contrast Management.
Namic's Burette System for Contrast Management.
Abbott's In–Line Burettes Sets.

*Primary Examiner*—Randall L. Green
*Assistant Examiner*—Perry E. Van Over
*Attorney, Agent, or Firm*—Kenyon & Kenyon

[57] ABSTRACT

An automatic flow regulator for use in a liquid management system is provided, as well as a method for its use. More particularly, a flow regulator and a method for its use are provided which can effectively regulate the flow of liquid in, e.g., an intravenous application. The flow regulator further provides de-bubbling features. For example, a deflector such as a dripdish and an air barrier are provided which serve to reduce the amount of bubbles in a liquid reservoir, greatly enhancing patient safety. The liquid may advantageously be an imaging liquid such as contrast.

18 Claims, 4 Drawing Sheets

U.S. PATENT DOCUMENTS

| | | |
|---|---|---|
| 4,941,875 | 7/1990 | Brennan . |
| 5,031,654 | 6/1991 | Kobayashi . |
| 5,032,112 | 7/1991 | Fairchild et al. . |
| 5,045,059 | 9/1991 | Theeuwes et al. . |
| 5,049,128 | 9/1991 | Duquette . |
| 5,059,173 | 10/1991 | Sacco . |
| 5,215,538 | 6/1993 | Larkin . |
| 5,236,417 | 8/1993 | Wallis . |
| 5,328,463 | 7/1994 | Barton et al. . |
| 5,334,170 | 8/1994 | Moroski . |
| 5,389,070 | 2/1995 | Morell . |

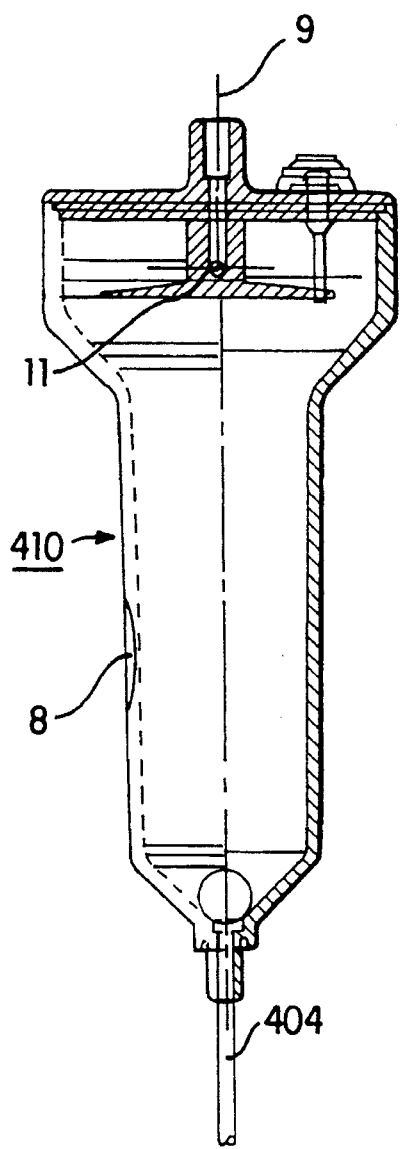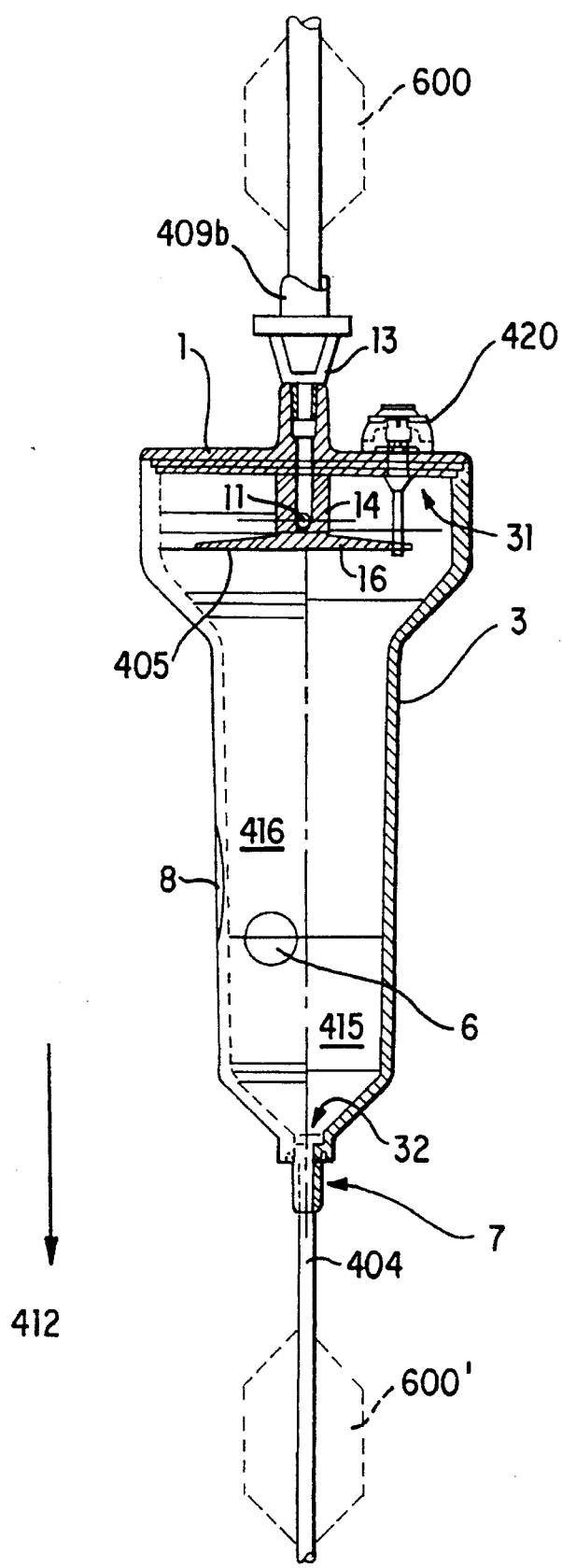
FIG. 2
FIG. 3

LIQUID REGULATOR AND METHOD OF USE

FIELD OF THE INVENTION

The invention relates to a regulator for the flow of liquid, as well as to a method for its use, and more particularly to a regulator for the flow of imaging liquid, such as contrast media, in a liquid management system. A regulator of the present invention may be advantageously used, for example, as part of an intravenous application.

BACKGROUND OF THE INVENTION

There are numerous medical procedures that involve the administration of relatively large volumes of liquid to a patient. Where such liquids are administered intravenously, it is essential that bubble-free sterile liquids be fed to the patient in controllable rates and quantities. The term "liquid management system" is used herein to denote various means for connecting a patient to a liquid source. One illustrative example of a liquid management system is an apparatus including a spike, tubing, valves, needle, etc., for establishing a liquid flow from a source to a patient for intravenous administration of an imaging liquid for angiography.

For many reasons, hospitals are becoming more aware of a need to reduce costs. One way in which savings may be achieved is by the conservation of medical intravenous liquids. As an example of such liquids, angiography procedures require the use of contrast media. These contrast media are radiopaque liquids that image vasculature.

In the past one container of liquid (contrast media) would typically be used for each procedure. After the procedure, the container was disposed of even if it was not empty. This wasteful procedure was required because of the danger of patient-to-patient contamination with the multiple use of a single container. That danger was present because of the bi-directional route of liquid flow between patient and container. The danger of patient-to-patient contamination can be avoided by eliminating the bi-directional flow, e.g., with a one-way valve, and disposing of any portion of the liquid management system that may have been in liquid communication with a previous patient's body fluids, e.g., everything downstream of and including the one-way valve.

To manage the flow of liquid to a patient, e.g., the quantity and rate of flow, various flow regulator devices have been incorporated into liquid management systems, for example, a burette. A burette can be filled with a desired amount of liquid, e.g., the quantity needed for a planned procedure. However, liquid flow through a burette may present several problems.

First, dropping liquid through an air-space into the base of a burette may lead to bubbling. Second, a relatively large amount of liquid must always be present in a burette, usually greater than 20 cc, in order to minimize the occurrence of bubbles. This requirement is due to several factors. A primary one is that if the level of liquid is too low, a drop containing a bubble may have enough momentum from its fall to tunnel through the liquid and enter the downstream tubing with the bubble intact. Another important factor is that the increased pressure at the base of a large amount of liquid tends to drive any bubbles towards the surface of the liquid, thus removing them from the base where the liquid enters the downstream tubing. An additional factor is that drawing larger quantities of liquid from a burette accidentally may cause the burette to become depleted of liquid, thus starting an undesirable intake of air into the tubing leading to the syringe. Third, filling a burette may increase the set-up time for a liquid management system significantly. Fourth, an operator must manually observe the liquid level in a burette and refill the burette periodically in order to prevent the liquid level from being depleted.

OBJECTS AND SUMMARY OF THE INVENTION

An object of the present invention is to provide a flow regulator which can cut off the flow of liquid when the container's contents are depleted, without incorrectly cutting off flow at other times during the procedure, thereby alerting the physician before air is drawn into the syringe. For example, although some intravenous drip chambers employ balls which float in the liquid to cut off flow on depletion, they are currently only applicable to slow infusions. At higher flow rates of 2 to 5 cc per second, which would typically be encountered in an imaging liquid management application, such balls can incorrectly shut off flow, especially since the ball typically is located directly underneath the dripping liquid. Thus, there is a need for a ball shut-off valve which is not encumbered by being in the direct line of the flowing liquid.

Another object of the present invention is to provide a flow regulator which would allow users to inject liquid back into a reservoir for purposes of debubbling the system. The flow regulator of this invention also reduces the amount of liquid necessary to avoid bubbles and has an automatic refilling feature.

The above objects and others are met by a flow regulator of the present invention. A flow regulator for liquid media is provided which includes a reservoir defined by walls. The flow regulator has a liquid inlet and a liquid outlet. The flow regulator further has a deflector in the path of the liquid, between the liquid inlet and the liquid outlet, so that the liquid exiting the liquid inlet is deflected towards the walls of the reservoir prior to passing through the liquid outlet.

A liquid management system for contrast media incorporating such a flow regulator preferably also has at least one means for establishing unidirectional flow, e.g., a check valve upstream of the liquid inlet to ensure that the liquid flows in a unidirectional manner and means for disconnecting all parts of the system that could be in liquid communication with a patient's body fluids. Such a system allows the same container of liquid to be used for more than one procedure.

The flow regulator may also have a ball seat substantially surrounding the reservoir liquid outlet, and a floating shut-off ball within the interior of the reservoir which closes the liquid outlet by engaging the seat when the level of the liquid is low due to the depletion of the contents of the reservoir.

The flow regulator may also have a vent valve. The vent valve allows for the filling of the reservoir because through it the system may be opened to the atmosphere. Gravity is utilized to pull the liquid into the reservoir. When a desired volume of liquid is in the reservoir, closing the vent valve stops or slows the downward flow of liquid because the residual air on top of the liquid has no path by which to escape. The vent is also opened when the liquid is drawn out, e.g., into a syringe. In this way, by opening the valve, air can displace the liquid which flows downstream to the syringe. Otherwise, if the valve is closed, the liquid does not flow easily because of the lack of fluid to replace it.

The flow regulator may further have a coupling boss for coupling the regulator to a liquid level sensor.

There is also disclosed a method of dispensing liquids using a flow regulator. The method preferably includes the steps of spiking a liquid container, filling a flow regulator with liquid, removing any bubbles from the liquid in the flow regulator, drawing liquid from the flow regulator into a syringe through a tube connected to the flow regulator liquid outlet, and injecting this drawn liquid into a catheter from the syringe. The amount of bubbling may be reduced by directing the liquid onto a deflector disposed in the reservoir which tends to direct the liquid substantially towards the interior walls of the reservoir. For example, a dripdish, a tube, a channel, a slide, or the like, may function as a deflector.

The deflector dissipates bubbles by increasing the surface area exposure of the liquid and by directing the liquid down the interior reservoir walls. A conical shape or tapering of the reservoir walls may also contribute to directing liquid down the interior reservoir walls by providing a larger surface area for the liquid drops to impact after they leave the deflector. A preferred deflector is a dripdish which generally includes a hollow neck, at least one side dispensing hole near the base of the neck, and a flange at the base of the neck. This flange may have a very gentle slope which serves to disperse liquid entering the reservoir towards the sides of the reservoir, and is generally located just below the dispensing hole. Alternately, a tube, channel, slide or the like which directs liquid onto the interior reservoir walls should also accomplish a similar result.

While the invention may be utilized to regulate the passage of any type of liquid, a preferred use of the flow regulator is in a liquid management system for an imaging liquid such as contrast media. In such an imaging liquid flow regulator, a requirement of the liquid is that it be generally capable of visualization in an appropriate diagnostic imager. For example, a radiopaque liquid would be suitable if an x-ray image were desired.

A typical use of the invention would be in an intravenous application. For example, often contrast media is injected into one or more blood vessels via a catheter to locate the blood vessels. Then the catheter is positioned in one of the vessels so located, and a larger amount of contrast media, substantially equal to that in a full syringe, is injected into a set of blood vessels via the catheter. An image is then taken of the vessels into which the liquid was injected. This procedure may be repeated until an acceptable image is taken. The image taken may be, for example, an x-ray image.

BRIEF DESCRIPTION OF THE DRAWINGS

FIG. 2 shows a cross-section of an embodiment of a flow regulator of the present invention, demonstrating a low liquid level situation.

FIG. 3 shows a cross-section of an embodiment of a flow regulator of the present invention, demonstrating its use with a check valve.

DETAILED DESCRIPTION

I. General Construction

A. Basic Configuration

Figure 1:
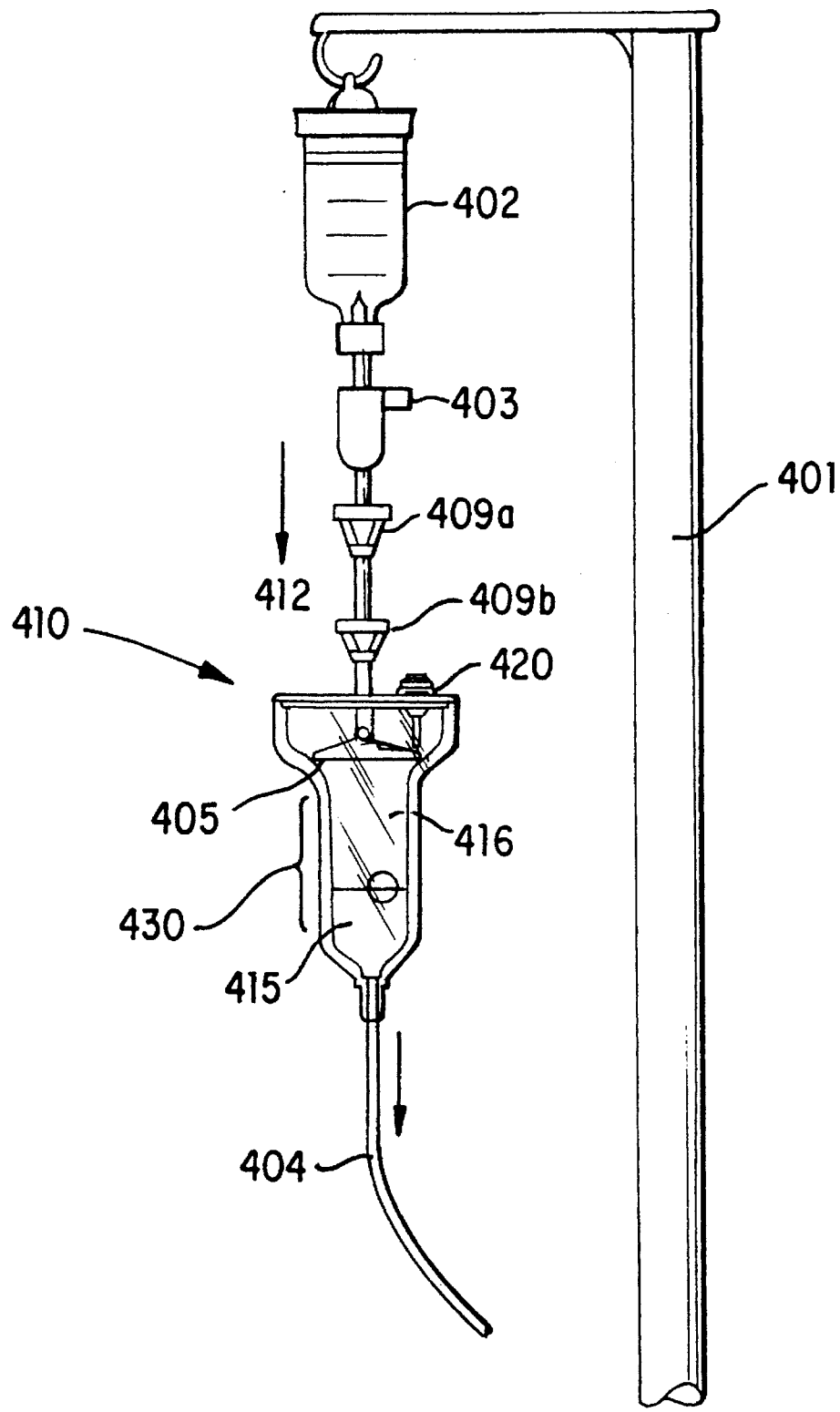
FIG. 1 illustrates an embodiment of a flow regulator of the present invention, showing its use in a liquid management system for angiography.

FIGS. 2 and 3 illustrate cross-sections of an embodiment of a flow regulator 410 of the present invention, while FIG. 1 illustrates its use in a typical angiography system.

FIG. 1 illustrates how a flow regulator 410 of the present invention may be configured within an overall system. A container 402 which holds a liquid is opened with a spike 403. The liquid is preferably an imaging liquid which is capable of visualization, such as a radiopaque liquid. For example, Hexabrix™ is commonly used. Located just downstream of spike 403 may be a stopcock (not shown). A tube leads from the stopcock to one, and preferably two, check valves 409a and 409b. It is between the stopcock and the first check valve that the system may be disconnected such that the container can be re-used in another procedure. By retaining the system upstream of this point and changing the system downstream of this point, sterility may be ensured because no patient contaminants can travel upstream of the check valves. After passage through the check valves 409a and 409b, the liquid flows downstream to the flow regulator 410. After the liquid passes through the flow regulator 410, the liquid enters a tube 404 and flows downstream to a catheter system.

Figure 6:
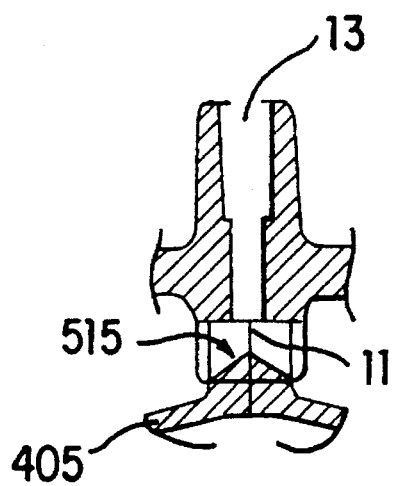
FIG. 6 shows an exploded section of FIG. 4, depicting, e.g., a liquid inlet.

FIG. 2 and FIG. 3 show a preferred embodiment of the flow regulator 410 in detail. In particular, FIG. 3 shows a reservoir 3 having a top opening 31 on the top and a second opening 32 on the bottom. The walls of the reservoir 3 may advantageously be made of a clear thermoplastic material such as polycarbonate. The reservoir 3 provides an air space above the liquid which is denoted herein as air space 416. For convenience, the liquid reserve contained in the reservoir 3 is denoted herein as liquid reserve 415. In the embodiment shown, the top opening 31 is covered with a cap 1, while the bottom opening 32 leads to a tube 404. The top opening 31 may preferably have a greater diameter than the bottom opening 32. In this way, the reservoir 3 has a generally tapered shape. The cap 1 has a fluid connection therethrough, with the upper connection shown as liquid inlet 13 and the lower connection, which empties onto a deflector such as a dripdish 405 and into the liquid reserve 415, shown as at least one side dispensing hole 11. Just prior to exiting the side dispensing hole 11, the liquid is incident on a tip 515, as seen in FIG. 6. This tip 515 serves to deflect and distribute substantially equal proportions of the liquid in radially out and then down the deflector.

This deflector 405 is shown in this embodiment as a dripdish; however, alternative deflectors may also be used, such as a tube, a channel, or a slide. The deflector 405 generally is suspended by a neck 14 from the cap 1. At the base of neck 14 is tip 515 and at least one side dispensing hole 11. Substantially perpendicular to the neck 14 and located below hole 11 is a gradually sloping flange 16. The liquid descends through the hollow neck 14, is distributed in a radial fashion by tip 515, and is emitted by at least one hole 11. The liquid then flows down the sides of the flange 16 and runs off the edge. The point where the liquid runs off the edge is radially far enough away from the axis of the reservoir 3 and the direction of liquid flow is sufficiently radially directed so that the falling liquid strikes the internal walls rather than dripping directly onto the liquid in the liquid reserve 415. For this purpose, it is noted that it is advantageous to construct reservoir 3 such that the diameter of its top opening is greater than the diameter of its bottom opening, thus creating walls which are tapered. It is particularly preferred that the internal walls slope radially inward in the region adjacent the periphery of the deflector 405 to help ensure that falling liquid strikes the reservoir walls. The deflector 405 may be manufactured integral with the tube defining the liquid inlet 13 through the cap 1. Its location is generally just below the side dispensing hole 11.

Figure 4:
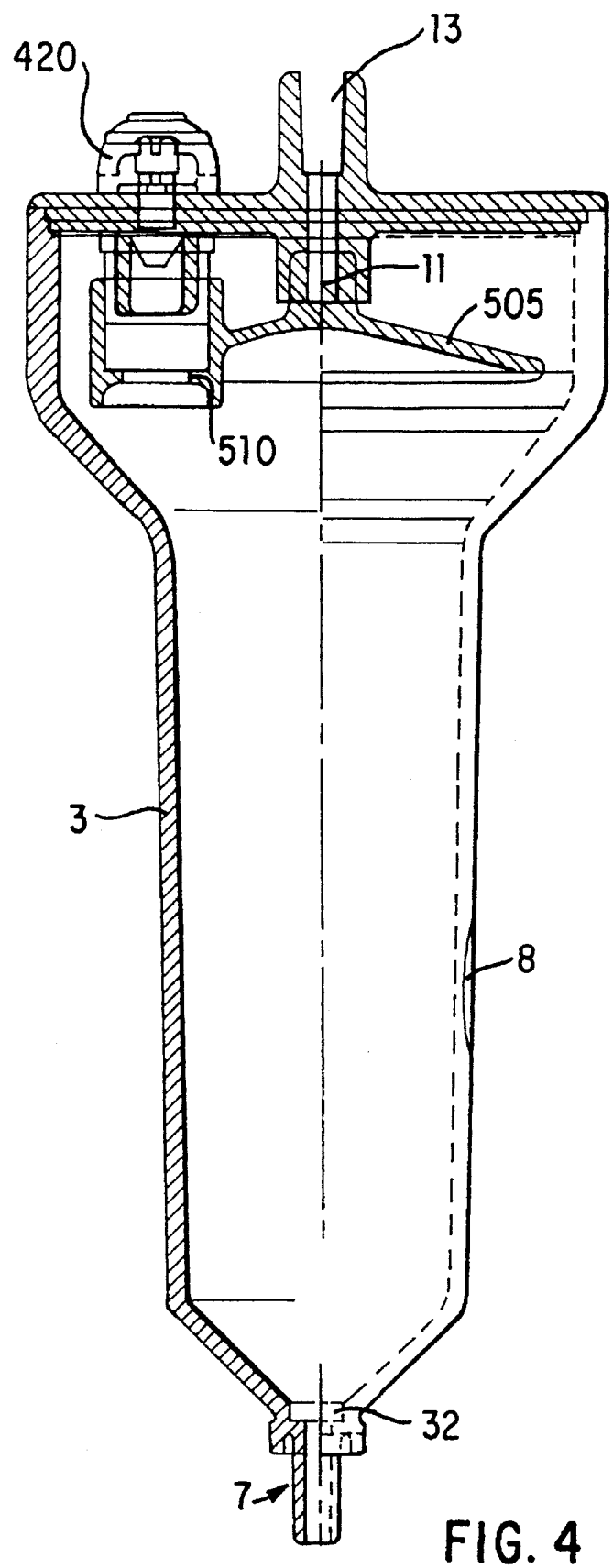
FIG. 4 shows a cross-section of an embodiment of a flow regulator of the present invention, demonstrating its use with a vent valve which is physically attached to the deflector.
Figure 5:
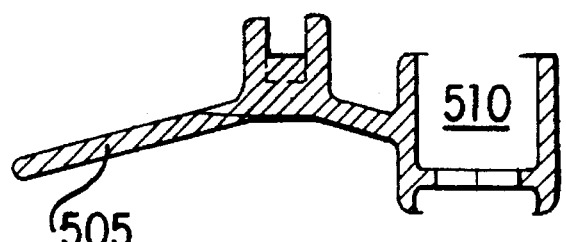
FIG. 5 shows a cross-section of the deflector in the embodiment of FIG. 4, illustrating a hole wherein part of the vent valve may be located.

FIGS. 4 and 5 show the construction of deflector 405 with air passage 510 therethrough. In this way, part of a vent valve 420 may be accommodated in a portion of the air passage 510. This allows air to more directly enter and exit the reservoir 3, and minimizes air stresses on the deflector 405.

B. Vent Valve

As shown in FIG. 4 a vent valve 420 is provided to open the system, which includes the reservoir 3, the cap 1, and the tube 404 which may be opened to the to atmosphere to permit air to enter into or escape from reservoir 3. This allows liquid to fall downward under the influence of gravity and fill the reservoir 3. Once a suitable level of liquid is present in the liquid reserve 415 of the flow regulator 410, as judged by the operator, the vent valve 420 may be closed, restricting the flow of any more liquid. The vent valve 420 preferably seals the system at pressures between about 30 psi and −10 psi, and is advantageously a one-touch vent valve. It is normally closed but can be mechanically overridden by depressing button 601.

Figure 7:
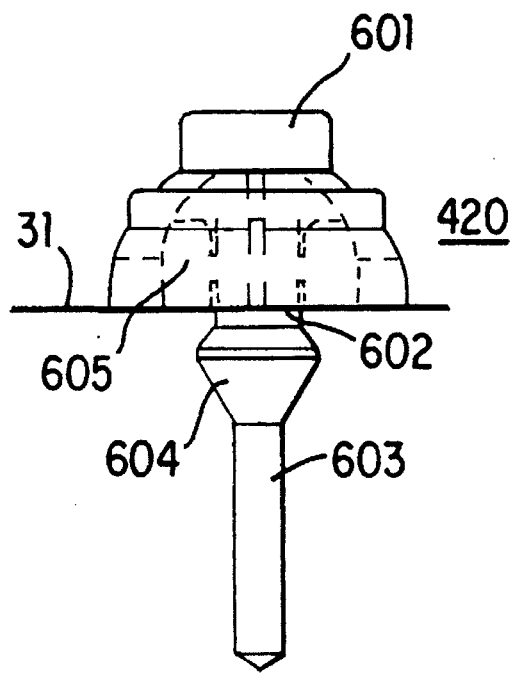
FIG. 7 shows an exploded section of the vent valve of FIG. 4.

An example of such a vent valve 420 is shown in FIG. 7. In this figure, button 601 is connected to upper shaft 602. Upper shaft 602 is connected to lower shaft 603 via stopper 604. A spring biasing means is provided between button 601 and cap 31 such that, when the button 601 is not depressed, the stopper 604 prevents air from passing from one side of the cap 31 to the other side. The spring biasing may be provided by the elasticity of button 601 itself or a separate spring (not shown) or the like. The volume surrounding upper shaft 602 is not air-tight, however, so that when the button 601 is depressed, thus forcing the stopper 604 out of engagement with the hole in the cap 31, a continuous fluid passageway is formed between the outside atmosphere and the interior of the flow regulator 410. When the continuous fluid passageway is formed, the pressure inside the flow regulator 410 equalizes to the pressure outside.

C. Optional Ball Shut-Off

The liquid reserve 415 in the reservoir 3 will be depleted when the level of liquid in the container 402 diminishes sufficiently. A floating shut-off ball 6 may be provided in the flow regulator 410 which floats on the liquid reserve 415. The ball 6 may be hollow and constructed of a material with a specific gravity less than one. When the liquid reserve 415 is depleted sufficiently, the ball 6 seals against a ball seat 7 located on the base of the reservoir 3. The ball 6 prevents any further liquid motion in the direction 412 from the container 402 to the tube 404. (This type of shut-off is well-known in the art.) However, its operation in the system of the present invention is particularly useful. This is because of the combined effect of the ball 6 and the manner in which the liquid flows down the sides of the reservoir 3.

The result is that the ball is not struck by the flow of liquid. In other systems, where no deflector 405 is used, the ball is often struck with a direct flow of dropping liquid. In a low liquid level situation, this may inappropriately force the ball 6 off of the seat 7. In a high liquid level situation, it may inappropriately force the ball 6 onto the seat 7. By the present invention, where the liquid flows down the walls, thus not directly striking the ball 6, stability of the ball is enhanced. Furthermore, after the liquid flows down the walls, its momentum, after reflecting from the liquid reserve 415, tends to be directed upwards. This buoys the ball 6 upward, preventing it from engaging the seat 7 until such time as the liquid reserve 415 is clearly depleted.

D. Coupling Boss

A coupling boss 8 may be provided on a side of the reservoir 3. Using such a boss 8, a liquid level sensor (not shown) can be coupled to the flow regulator 410 to automatically sense the amount of liquid left in the liquid reserve 415. The boss 8 is used so that the sensor may better sense the amount of liquid left in the liquid reserve 415. Not shown in the diagrams but inherent therein is the possibility of coupling the flow regulator to a computer-assisted apparatus which may be used to control the flow of liquid using data obtained from the liquid level sensor.

E. Flow Meter

In another embodiment, one or more flow meters may be incorporated in the system. It will be appreciated that flow could be measured by any appropriate means well-known in the art, for example, any appropriate electromechanical device. The position of such a flow meter is exemplified in FIG. 3 as dotted elements 600 and 600'. Meter 600 would measure the flow rate between the container 402 and the flow regulator 410, while meter 600' would measure the flow rate in the tube 404. In either case, the flow meter would typically be connected to a counter or a process controller, and would measure the volumetric flow per unit time and display that volume on a display unit. Typical flow meters are available from, e.g., Digiflow Systems, and include the DFS series flow meters.

II. Method of the Invention

The method of the present invention includes spiking the container 402 with spike 403, as shown in FIG. 1. The system, which is normally sealed from the atmosphere, does not immediately allow liquid to flow. Depressing the vent valve 420 opens the system to atmosphere, which then causes liquid to descend from the container 402 via gravitational influences. The liquid, which is typically some type of contrast, then passes through check valves 409a and 409b and into the flow regulator 410 via liquid inlet 13. In this manner the flow regulator 410 fills with liquid while bubbles are removed from the liquid. The bubbles, for example, may arise because pockets of air within the components of the system become dislodged as the liquid flows downstream past these components, drawing the pockets of air into the liquid as air bubbles. The check valves only allow liquid flow in one direction, as shown by the arrow 412, and of course, inhibit the passage of contaminants from the patient to the container 402. This characteristic, at least in part, allows the multiple use of a single container of liquid. In particular, when the tubing is changed to allow the multiple use of a single container of liquid, it is changed upstream of the check valves 409. In this way, contaminants from the patients can only reach those portions of the system which are changed before re-use, thus ensuring sterility.

Bubbles are removed in this method in several concurrent ways. Two features of the flow regulator 410 tend to reduce the dangerous occurrence of bubble formation in the liquid reserve 415. First, the liquid passes over a large surface area; second, the liquid is deposited into the liquid reserve 415 in a substantially nonturbulent manner. In particular, the liquid enters the liquid inlet 13 and exits the side dispensing hole 11 onto the deflector 405. Prior to exiting the side dispensing hole, however, the liquid impinges on deflector tip 515, as indicated in FIG. 6. This tip 515 serves to direct substantially equal proportions of the liquid in all radial directions down the deflector 405. In this way, the liquid is spread into a thin layer. As the liquid is deflected by the deflector 405 onto the sides of the reservoir 3, its surface area again increases because it spreads out as it passes down the sides of the reservoir 3. As such, any bubbles present in the liquid are on or near a surface, and are therefore more likely to break. Therefore, passage of the liquid down the sides of the reservoir, through air barrier 416, tends to reduce the total amount of bubbles. Finally, the deflector 405 stops the liquid from vigorously plunging into the liquid reserve 415 below, thus further reducing the amount of bubbling. Other similar deflector mechanisms could also be used. For example, a tube, a channel, or a slide could accomplish a similar result.

However the bubbling is reduced, liquid is then drawn through the tube 404 which is connected to the liquid outlet of flow regulator 410, into a syringe, directly or by using a valued manifold (not shown in this figure). The liquid in the syringe may then be injected into a catheter, which is connected by a manifold tubing to the syringe. The catheter is typically placed in the vasculature of the patient.

When the supply of liquid in the container 402 is depleted, the amount of liquid in the reservoir 3 may also become depleted. When the liquid in reservoir 3 is depleted, the ball 6 will descend and eventually seal against the seat 7, as shown in FIG. 2. When the ball 6 seals against the seat 7, there should still be a sufficient amount of liquid present in the tube 404 to prevent formation of air bubbles. For example, typically about 10 cc will be present. Due to the ball 6 sealing against the seat 7, and the continuous amount of liquid between the ball and the syringe (10 cc), the syringe will be unable to draw any additional liquid. More particularly, the syringe cannot draw any more liquid because there is no fluid, either gas or liquid, available to fill the space vacated by any liquid the syringe might draw. This feature acts as a notice to the physician that the flow regulator has been depleted of its liquid contents. It also, and perhaps more importantly, serves to avoid inadvertent drawing of air into the syringe which could lead to embolism formation in the patient.

In a typical use of a flow regulator 410 of the present invention, small amounts of liquid are injected into a set of blood vessels to locate where the blood vessels are. Once a physician views an image of the vasculature, he or she chooses a particular area to examine more fully. The catheter may be replaced so as to better view the area, followed by the injection of a full syringe of liquid. The image may then again be taken, as is well-known in angiography procedures. This procedure may be repeated until the physician is satisfied that all the relevant imaging has been accomplished, or until the supply of liquid in the container 402 is depleted.

Those skilled in the art will understand that the various optional features of the disclosed flow regulator and method of its use may be combined in any number of ways in an overall system without departing from the scope of the present invention. In addition, any number of liquids may be used in the present invention. The invention is to be limited only by the claims appended hereto.

What is claimed is:

1. A flow regulator for liquids, comprising:
   a. a reservoir having walls, a liquid inlet and a liquid outlet;
   b. a deflector disposed so that a liquid entering the reservoir via the liquid inlet is deflected towards the reservoir walls; and
   c. a vent in fluid communication with the reservoir.

2. The flow regulator of claim 1, wherein the vent comprises a normally closed, mechanically actuated valve.

3. The flow regulator of claim 2, wherein the deflector comprises a dripdish.

4. The flow regulator of claim 2, wherein the deflector is selected from the group consisting of a tube; a channel; and a slide.

5. The flow regulator of claim 3, wherein the walls of the reservoir are tapered radially inwardly, in a direction from the liquid inlet to the liquid outlet.

6. A system for regulating the flow of liquids, comprising:
   a. a first tubing section having a proximal end and a distal end, a first fluid connector disposed at the proximal end of the first tubing section for connection to a liquid source, and a second fluid connector disposed at the distal end of the first tubing section;
   b. a flow regulator comprising: a reservoir having walls, a liquid inlet and a liquid outlet; a deflector disposed so that a liquid entering the reservoir via the liquid inlet is deflected towards the reservoir walls; and a vent in fluid communication with the reservoir;
   c. a second tubing section having a proximal end and a distal end, wherein the distal end of the second tubing section is connected to the liquid inlet of the reservoir;
   d. a third fluid connector disposed at the proximal end of the second tubing section, wherein the third fluid connector is engageable with the second fluid connector;
   e. liquid control means for controlling the flow of liquid into the flow regulator, wherein the liquid control means is disposed in the first tubing section or the second tubing section;
   f. one-way liquid flow means disposed in the second tubing section, for preventing liquid flow through the tubing in a direction from the flow regulator toward the liquid source;
   g. a third tubing section having a proximal end and a distal end, wherein the proximal end of the third tubing section is connected to the liquid outlet of the reservoir; and
   h. a fourth fluid connector disposed at the distal end of the third tubing section.

7. The liquid regulating system of claim 6, wherein the vent comprises a normally closed, mechanically actuated valve.

8. The liquid regulating system of claim 7, wherein the deflector comprises a dripdish.

9. The liquid regulating system of claim 7, wherein the deflector is selected from the group consisting of a tube; a channel; and a slide.

10. The liquid regulating system of claim 8, wherein the walls of the reservoir are tapered radially inwardly in a direction from the liquid inlet to the liquid outlet.

11. The liquid regulating system of claim 10, wherein the first liquid connector comprises a vented spike.

12. The liquid regulating system of claim 11, wherein the one-way liquid flow means comprises at least one, one-way check valve.

13. The liquid regulating system of claim 12, wherein the liquid control means comprises a stopcock.

14. The liquid regulating system of claim 13, wherein the liquid comprises contrast media suitable for use in an angiographic procedure.

15. The liquid regulating system of claim 13, further comprising a flow meter for detecting the amount of contrast media passing through the flow regulator.

16. A method of administering liquid using the liquid regulating system of claim 6, comprising the steps of:

a. connecting the first tubing section to the liquid source;

b. connecting the fourth fluid connector to a manifold having a syringe engageable therewith;

c. connecting the first tubing section to the second tubing section by engaging the second fluid connector with the third fluid connector;

d. opening the liquid control means;

e. opening the vent, thereby opening the reservoir to the atmosphere and allowing liquid from the container to flow into the reservoir;

f. filling the reservoir to a suitable level with liquid from the liquid source, wherein the liquid entering the reservoir is deflected by the dripdish toward the reservoir walls;

g. closing the vent, thereby closing the reservoir to the atmosphere and stopping liquid from flowing into the reservoir;

h. drawing liquid into the syringe engaged with the manifold, thereby creating a negative pressure in the reservoir and causing the reservoir to automatically refill to the suitable level with liquid from the liquid source; and i. injecting liquid from the syringe into a patient.

17. A method of administering liquid using the liquid regulating system of claim 6, comprising the steps of:

a. connecting the first tubing section to the liquid source;

b. connecting the fourth fluid connector to a manifold having a syringe engageable therewith;

c. connecting the first tubing section to the second tubing section by engaging the second fluid connector with the third fluid connector;

d. filling the reservoir to a suitable level with liquid from the liquid source, wherein the liquid entering the reservoir is deflected by the dripdish toward the reservoir walls;

e. drawing liquid into the syringe, and injecting the liquid from the syringe into a first patient;

f. disconnecting the first tubing section from the second tubing section by disengaging the second fluid connector from the third fluid connector;

g. discarding the second tubing section, the flow regulator, the third tubing section, the manifold and the syringe, and retaining the first tubing section and the liquid source for use in a subsequent procedure;

h. connecting the first tubing section to a second, sterile second tubing section that is connected to a second, sterile flow regulator, and second, sterile third tubing section and second, sterile manifold; and i. administering liquid from the liquid source to a second patient in a subsequent procedure.

18. The method of claim 17, wherein step e. is performed more than one time prior to the performance of step f.

* * * * *